(12) United States Patent
Glowacki et al.

(10) Patent No.: US 7,744,567 B2
(45) Date of Patent: Jun. 29, 2010

(54) REDUCING WITHDRAWAL FORCE IN A SAFETY IV CATHETER

(75) Inventors: Kristoffer Glowacki, Staffanstorp (SE); Johan Fredrik Thörne, Helsingborg (SE); Lars-Åke Lennart Larsson, Lund (SE); Jörgen Bruno Hager, Helsingborg (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 198 days.

(21) Appl. No.: 11/943,341

(22) Filed: Nov. 20, 2007

(65) Prior Publication Data

US 2009/0182280 A1 Jul. 16, 2009

Related U.S. Application Data

(60) Provisional application No. 60/867,041, filed on Nov. 22, 2006.

(51) Int. Cl.
*A61M 5/178* (2006.01)

(52) U.S. Cl. .................. 604/164.08; 604/110; 604/111; 604/164.01; 604/164.06; 604/164.07

(58) Field of Classification Search ................. 604/110, 604/164.01–164.12, 168.01, 265
See application file for complete search history.

(56) References Cited

U.S. PATENT DOCUMENTS

| | | | |
|---|---|---|---|
| 4,929,241 A | 5/1990 | Kulli | |
| 4,952,207 A | 8/1990 | Lemieux | |
| 5,053,017 A | 10/1991 | Chamuel | |
| 5,279,591 A | 1/1994 | Simon | |
| 5,562,633 A | 10/1996 | Wozencroft | |
| 5,697,907 A | 12/1997 | Gaba | |
| 5,718,688 A | 2/1998 | Wozencroft | |
| 5,853,393 A | 12/1998 | Bogert | |
| 5,919,172 A * | 7/1999 | Golba, Jr. | 604/272 |
| 6,117,108 A * | 9/2000 | Woehr et al. | 604/110 |
| 6,203,527 B1 * | 3/2001 | Zadini et al. | 604/110 |
| 6,322,537 B1 * | 11/2001 | Chang | 604/164.08 |
| 6,981,965 B2 | 1/2006 | Luther et al. | |
| 7,186,239 B2 | 3/2007 | Woehr | |
| 7,214,211 B2 | 5/2007 | Woehr et al. | |
| 7,226,434 B2 | 6/2007 | Carlyon et al. | |
| 7,264,613 B2 | 9/2007 | Woehr et al. | |
| 2002/0169418 A1 | 11/2002 | Menzi et al. | |
| 2003/0032927 A1 | 2/2003 | Halseth et al. | |
| 2003/0144627 A1 | 7/2003 | Woehr et al. | |
| 2004/0010227 A1 | 1/2004 | Riesenberger et al. | |
| 2004/0215154 A1 | 10/2004 | Hwang et al. | |
| 2004/0243061 A1 * | 12/2004 | McGurk | 604/164.08 |
| 2006/0079844 A1 | 4/2006 | Whisson et al. | |
| 2006/0270980 A1 | 11/2006 | Menzi et al. | |

(Continued)

*Primary Examiner*—Nicholas D Lucchesi
*Assistant Examiner*—Leah Stohr
(74) *Attorney, Agent, or Firm*—Mony R. Ghose; Craig Metcalf; Kirton & McConkie

(57) ABSTRACT

An extravascular system for accessing the vasculature of a patient may include a catheter adapter, a needle, and/or a needle tip shield assembly. The needle tip shield assembly may have a needle cap, and the needle cap may have a needle shield and at least one low friction surface. The needle may be disposed within the catheter assembly and the needle tip shield assembly. The low friction surface may reside between the needle shield and the needle. The at least one low friction surface may reside on the needle, on the V-clip, and/or on a structure located between the needle and the V-clip.

11 Claims, 6 Drawing Sheets

U.S. PATENT DOCUMENTS

2007/0038188 A1* 2/2007 Bialecki et al. ........ 604/164.08
2007/0161950 A1 7/2007 Carlyon et al.
2007/0179447 A1 8/2007 Carrez et al.

* cited by examiner

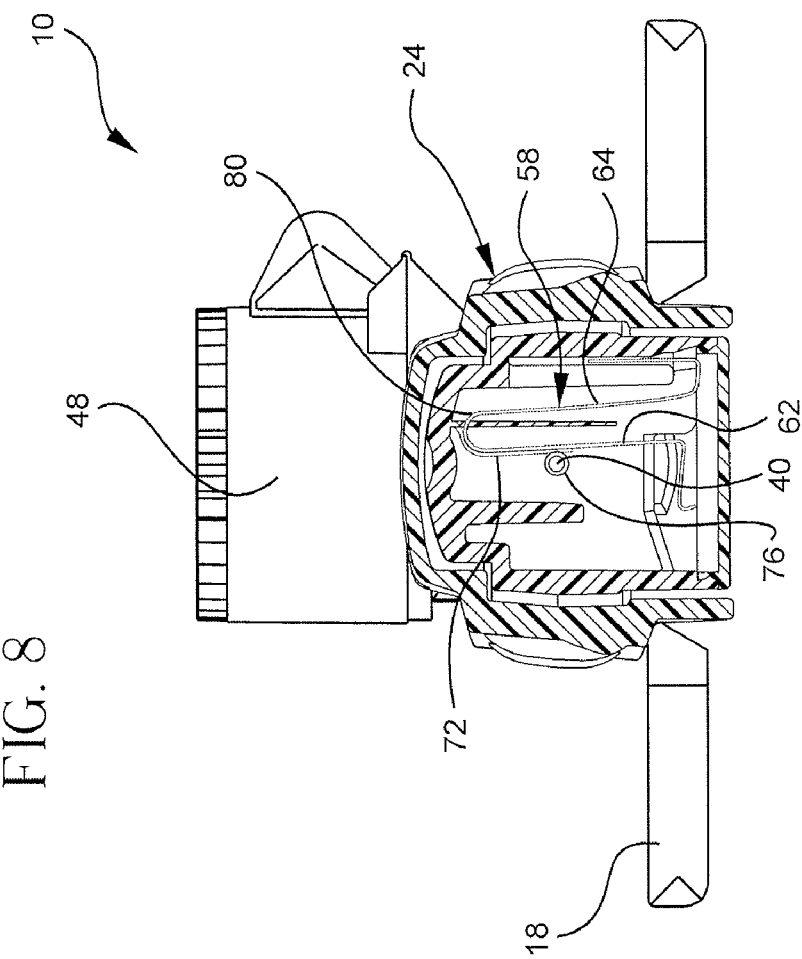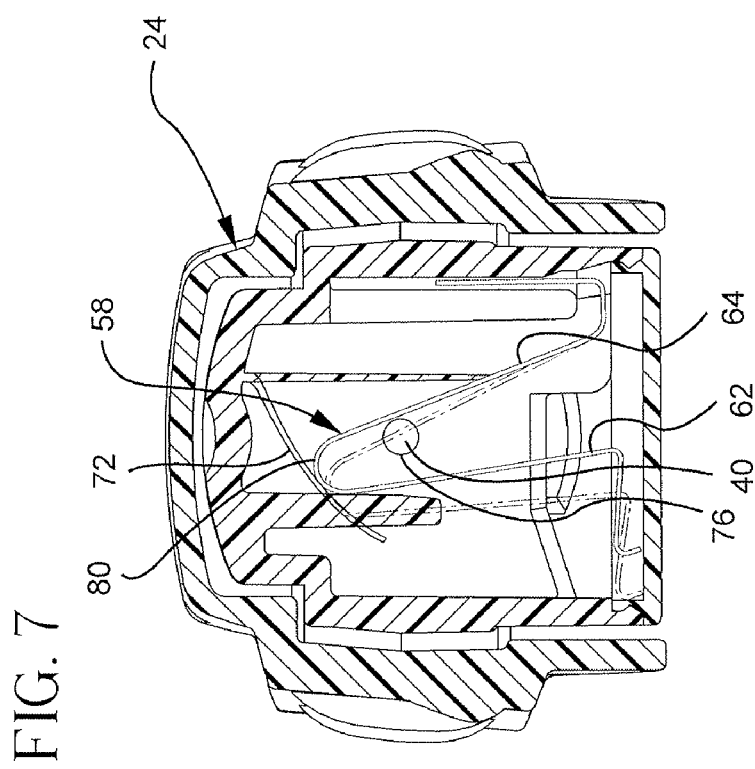

REDUCING WITHDRAWAL FORCE IN A SAFETY IV CATHETER

RELATED APPLICATIONS

This application claims the benefit of U.S. Provisional Application No. 60/867,041, filed Nov. 22, 2006, entitled REDUCING WITHDRAWAL FORCE IN A SAFETY IV CATHETER, which is incorporated herein by reference.

BACKGROUND OF THE INVENTION

This invention relates generally to extravascular systems and methods, including catheter assemblies and devices used with catheter assemblies. Generally, extravascular systems are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber in the extravascular system. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield device that covers the needle tip and prevents accidental needle sticks. In general, a needle shield includes a housing, a sleeve, or other similar device that is designed such that when the needle is withdrawn from the patient, the needle tip will be trapped/captured within the needle tip shield. The purpose of these needle tip shield devices is to house the tip of the needle in a secure location, thereby avoiding the possibility of needle sticks after the needle and needle shield device are separated from the catheter, which is left in place to provide intravenous access to the patient. As the introducer needle is withdrawn from the patient, the needle grates or otherwise causes friction as it slides past the metal components within the needle tip shield device. Thus, various systems and methods are needed to provide needle tip shields that decrease the withdrawal force required and friction caused as a needle is withdrawn through a needle tip shield device.

BRIEF SUMMARY OF THE INVENTION

The present invention has been developed in response to problems and needs in the art that have not yet been fully resolved by currently available vascular access systems and methods. Thus, these systems and methods are developed to provide needle tip shields that decrease the withdrawal force required and friction caused as a needle is withdrawn through a needle tip shield device.

An extravascular system for accessing the vasculature of a patient may include a catheter assembly, a needle, and/or a needle tip shield assembly. The needle tip shield assembly may have a needle cap, and the needle cap may have a needle shield and at least one low friction surface. The needle may be disposed within the catheter and the needle tip shield assembly. The low friction surface may reside between the needle shield and the needle.

The needle shield may be a V-clip. The V-clip may include a first arm and a second arm joined by an elbow. The at least one low friction surface may reside on the needle, on the V-clip, and/or on a structure located between the needle and the V-clip.

The structure may be secured to the needle cap, may be integral to the needle cap, and/or may include a fin. The needle cap may define a space where the fin may reside after the V-clip is engaged.

The at least one low friction surface may include a lubricant, a polymer, polytetrafluoroethylene (such as Teflon), and/or a soft metal. The low friction surface may be adhered to an adjoining structure, may be molded, and/or may include a surface with smooth edges. The surface may be included on a surface of a secondary structure, such as the fin mentioned above. The surface may be a surface of the V-clip. Alternatively, the needle itself may be a low friction surface.

A method of manufacturing an extravascular system for accessing the vasculature of a patient may include providing a catheter assembly, providing a needle, disposing the needle within the catheter assembly, providing a needle tip shield assembly having a needle cap, the needle cap having a V-clip, disposing the V-clip at least partially within the needle cap, and/or preparing at least one low friction surface between the V-clip and the needle.

The method may also include forming the needle shield as a V-clip having a first arm joined to a second arm by means of an elbow. The method may also include decreasing the withdrawal force and friction of the needle as it is drawn past the V-clip. The method may also include withdrawing the needle past the V-clip, engaging the V-clip, moving the first arm beyond the hole through which the needle was withdrawn, moving the low friction surface beyond the hole through which the needle was withdrawn, and/or resting the low friction surface within a space defined by the housing of the needle cap. Alternatively, the needle itself may be made with, or coated by, a low friction material.

An extravascular system for accessing the vasculature of a patient may include a catheter means, a needle means, and a needle tip shield assembly means. The needle tip shield assembly means may have a needle cap means. The needle cap means may have a means for shielding a needle and means for providing low friction. The needle means may be disposed within the catheter means and within the needle tip shield assembly means. The means for providing low friction may reside between the means for shielding a needle and the needle means.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention. BRIEF DESCRIPTION OF THE SEVERAL VIEWS OF THE DRAWINGS In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 7 is a cross section simulation view continued from the simulation of FIG. 6.

FIG. 8 is a cross section view of a catheter assembly.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
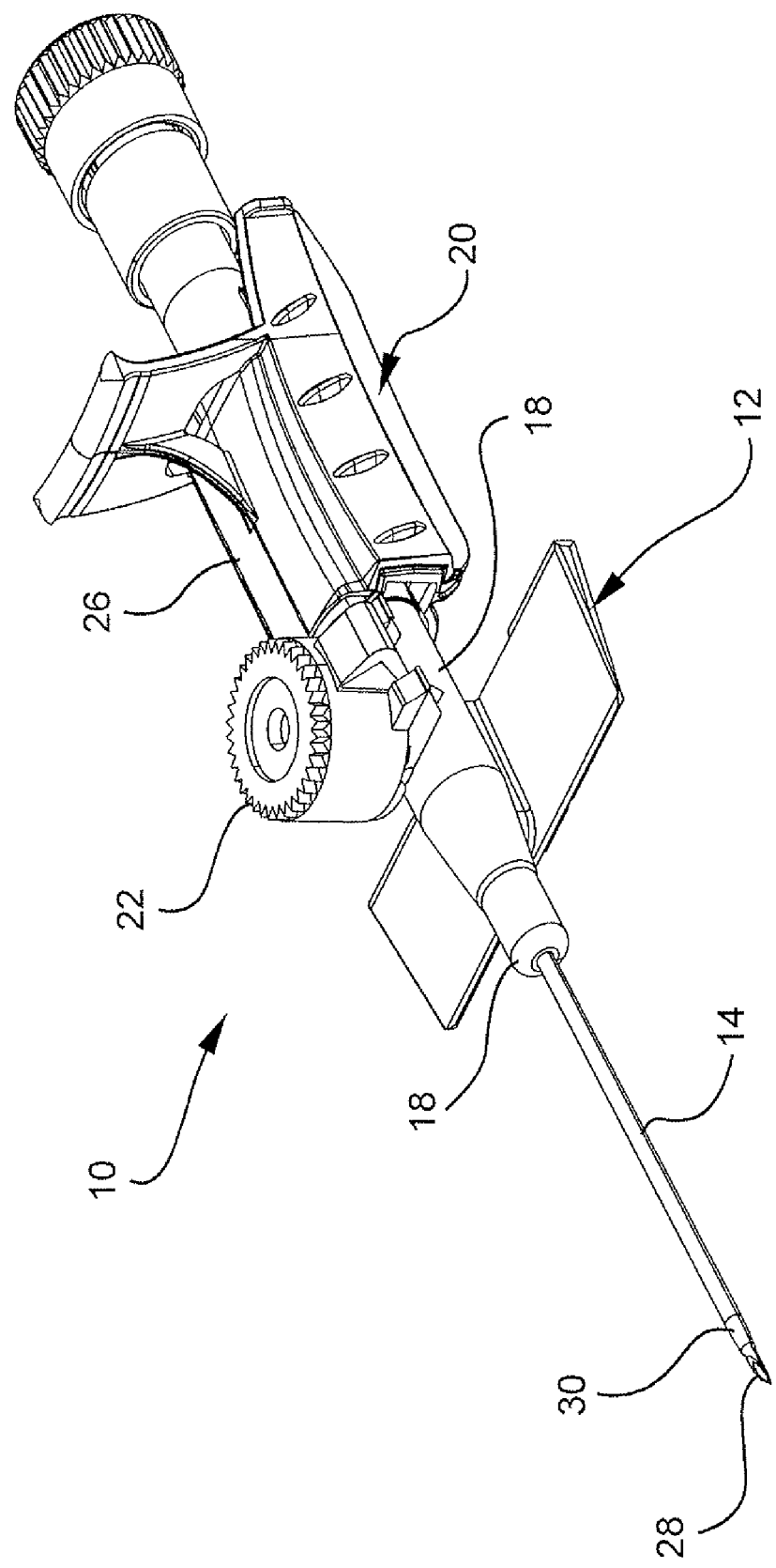
FIG. 1 is a perspective view of a extravascular system.

Referring to FIG. 1, a perspective view illustrates an example of an extravascular system 10 of multiple extravascular systems. In this example the extravascular system 10 includes a catheter assembly 12 and a needle assembly 20. The catheter assembly 12 includes a vascular access device, such as a catheter 14, partially housed within a catheter adapter 18. Also illustrated in FIG. 1 is a protection cap 22 positioned above the catheter adapter 18. The protection cap 22 may cover an access port which provides access into the catheter 14.

Figure 2:
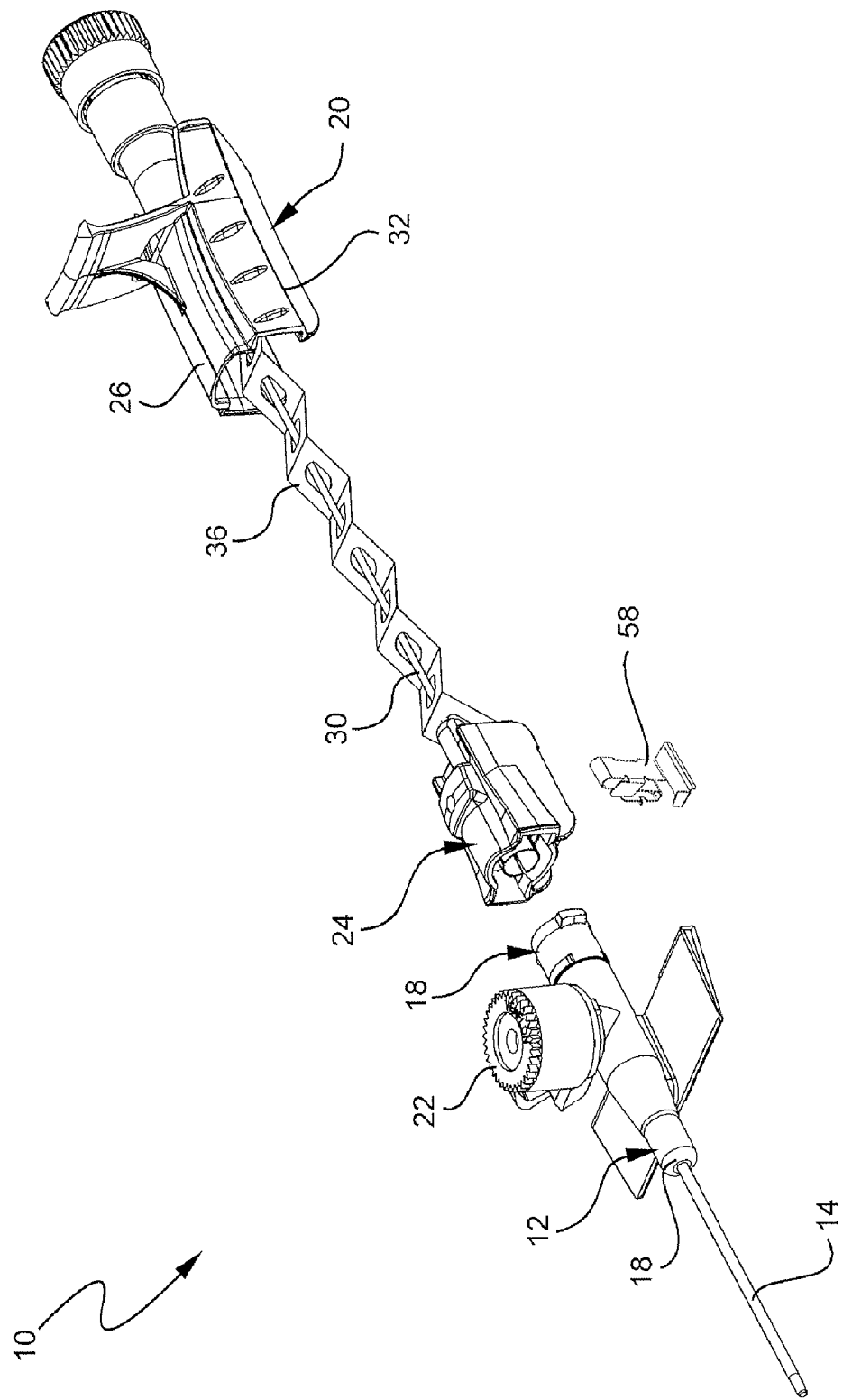
FIG. 2 is an exploded view of the extravascular system of FIG. 1.

Referring now to FIGS. 1 and 2, the extravascular system 10 also includes a needle assembly 20. The needle assembly includes a needle cap 24 and a needle hub 26. As can be seen by comparing FIGS. 1 and 2, the needle cap 24 and the tether 36 may be adapted to fit at least substantially inside the needle hub 26 when the needle assembly 20 is in the pre-use configuration. The needle assembly 20 may include additional parts or components adapted to provide the needle assembly 20 with the desired functionality. Similarly, the catheter assembly 12 may include additional or alternative parts and subcomponents depending on the configuration of the catheter assembly 12 and its intended usage.

The needle cap 24 is configured such that it will contain the needle tip 28 when the needle 30 is removed from the catheter 14. The needle assembly 20 is securely attached to the catheter adapter 18 thereby providing for manipulation of the needle 30 and placement of the catheter 14 within the vasculature of a patient. The needle assembly 20 may include grips 32 which allow for more secure gripping of the needle assembly 20 and maneuvering of the needle 30.

Referring now to FIG. 2, the extravascular system 10 is illustrated in an exploded view. As with FIG. 1, the catheter assembly 12 and needle assembly 20 are shown. As discussed above, the catheter assembly 12 includes a catheter 14 for placement within the vascular system of a patient. The catheter adapter 18 is configured such that the catheter 14 can be attached to further medical devices or tubing, such as for the administration of fluids to the patient. In that regard, the illustrated catheter assembly 12 also includes a protection cap 22 which covers an access port which provides further access to the catheter 14.

Also illustrated in FIG. 2 is the needle assembly 20 in a position in which the needle cap 24 has been fully separated from the catheter adapter 18. As mentioned above, the needle assembly 20 as illustrated includes grips 32 for use in retracting and manipulating the position of the needle 30.

Extending between the needle cap 24 and the needle hub 26 is a tether 36. The length of the tether 36 is selected such that when the needle cap 24 is maximally deployed from the needle hub 26 and the needle tip 28 of needle 30 is securely housed within the needle cap 24, the tether 36 is fully extended thereby preventing a separation of the needle cap 24 from the needle hub 26. Additionally, when the tether 36 is fully extended needle cap 24 is unable to be removed from the needle tip 28 thereby ensuring that the needle tip 28 remains safely contained within the needle cap 24. The tether 36 may be folded in an accordion configuration, may be straight, or take any other desired configuration.

As illustrated in FIG. 2, the needle tip 28 is secured within the needle cap 24. The tether 36 is in the extended position between the needle cap 24 and the needle hub 26. Thus, the needle 30 is prevented from being pulled out of the needle cap 24. The interior of the needle cap 24 also cooperates with structures on the needle (not shown) and the V-clip 58 to prevent the needle from moving forward out of the needle cap 24. The needle shield and/or V-clip 58 is illustrated in FIG. 2 in a contracted form; also illustrated is the clip housing cover 60, both of which are described in further detail below.

With continued reference to FIG. 2, during use of the catheter assembly 10, a clinician or operator of the catheter assembly 10 will withdraw the needle 30 from the vasculature of a patient while the needle cap 24 remains in a relatively stationary position. As the needle cap 24 remains in a stationary position, the outer surface of the needle 30 is drawn across the face of the first arm 62 of the V-clip 58, creating friction and/or an unpleasant grating sensation between the metal of the needle 30 and the metal and/or sharp edges of the first arm 62. In order to reduce the withdrawal force necessary to move the outer surface of the needle 30 across the face of the first arm 62, a different interface between the face of the first arm 62 of the V-clip 58 and the outer surface of the needle 30 is preferred.

Figure 3:
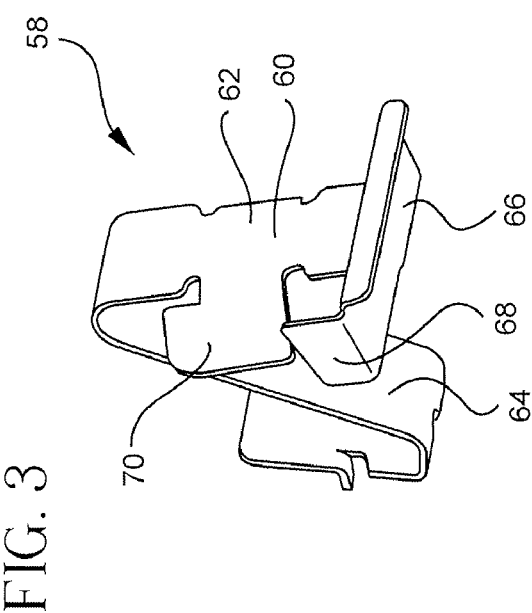
FIG. 3 is a perspective view of a V-clip with low friction coating.

Referring now to FIG. 3, the metallic face of the first arm 62 of the relaxed V-clip 58 has been coated with a low friction material 60. FIG. 3 also illustrates an extension 66 forming pawl 68. Furthermore a shield flap 70 is illustrated, which is structured such that it is capable of preventing reemergence of the withdrawn needle 30. The low friction material 60 is a material having a low friction coefficient such as a polymer or other layer added to the metal surface of the first arm 62. The additional material added to the surface of the first arm 62 changes the friction factor and has the potential to eliminate grating between the face of the first arm 62 and the outer surface of the needle 30. The low friction material 60 and/or barrier may be glued, using adhesive such as Loctite glue, insert molded, or coated with a polytetrafluoroethylene (Teflon), soft metal, and/or polymeric material. Additionally and/or alternatively, any lubricant may be placed on the surface of either the needle 30 and/or the face of the first arm 62. Chemically and/or physically reactive lubricants that cure under ultraviolet energy, heat, or other energy may be used to improve the coating properties of any surface involved in the communication of the needle 30 with the V-clip 58. The shape of the face 62 may also be modified such that there is minimal contact surface between the face of the first arm 62 and the surface of the needle 30. Additionally and/or alternatively, the mating surfaces of the face of the first arm 62 and/or the needle 30 may be rounded at the edges in order to provide a smooth mating surface that is not likely to cause grating and/or unnecessary friction caused by the edges of the two surfaces.

Any low friction material may be placed on any surface of the V-clip 58 that comes into contact with the surface of a needle 30. Additionally and/or alternatively, as illustrated in FIG. 2, a low friction surface 60 may be formed on the outer surface of the needle. Additionally and/or alternatively, a structure, membrane and/or material, such as a fin and/or sheet of material may be placed in between the V-clip 58 and the needle 30. The sheet of material between the V-clip 58 and the needle 30 may be integral to and/or mounted to any portion of the needle cap 24.

Figure 4:
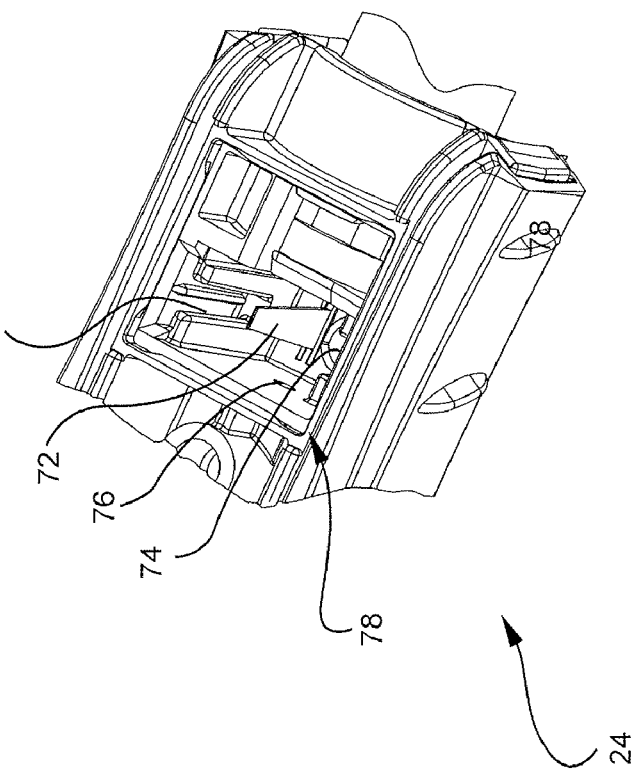
FIG. 4 is a bottom perspective view of a portion of a needle cap.

Referring to FIG. 4, the underside of the needle cap 24 is illustrated wherein the housing cover 60 has been removed thereby illustrating the interior of the V-clip housing 78. As illustrated, one embodiment described herein capable of reducing the withdrawal force of a needle 30 from the V-clip 58 (not shown) may include a thin member such as a fin 72 protruding from a portion of the needle cap 24. The fin 72 may be formed of the same material as the remainder of the needle cap 24 and/or may comprise another material selected for a low friction coefficient. A fin window 74 may be formed on the interior of the housing 78 adjacent to the fin 72 in order to provide a space within which the fin 72 may rest when the fin 72 is moved by the first arm 62 of a V-clip 58 (not shown).

The fin 72 will preferably be located and/or secured to the interior of the housing 78 of the needle cap 24 such that the fin 72 may be position between the needle 30 and the V-clip 58 when the V-clip 58 is compressed and placed in the shield mounting pocket 90. The needle 30 (not shown) intersects the housing 78 and extends through the needle port 76 wherein the fin 72 is pinched between first arm 62 of the V-clip 58 (not shown) and the needle 30 (not shown). As so configured, the fin 72 will function as low friction member between the needle 30 and the first arm 62 of the V-clip 58 thereby reducing and/or eliminating the withdrawal force of the needle 30 as well as any grinding sensation as experienced with the prior art.

Figure 5:
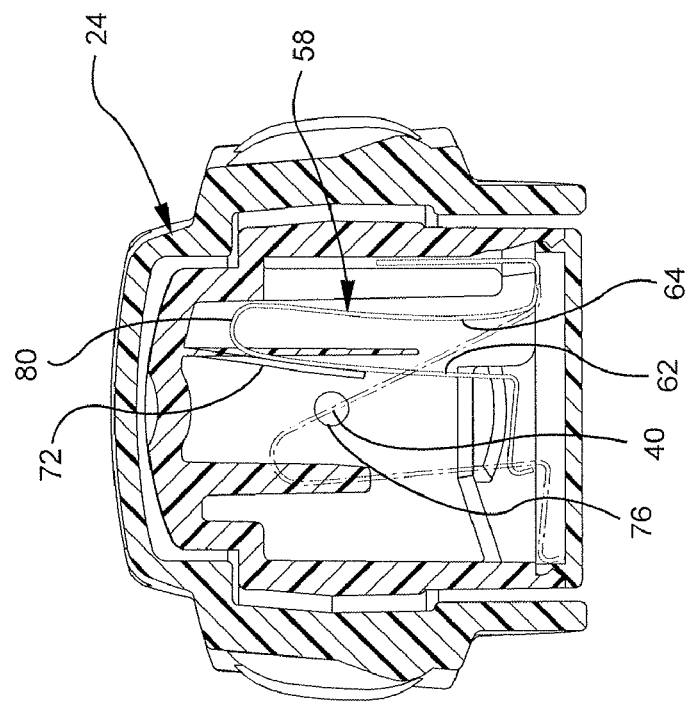
FIG. 5 is a cross section view of a portion of a needle cap.

Referring to FIG. 5, a side cross section view of a needle cap 24 is shown. The side cross section view reveals the fin 72 protruding from the housing 78 of the needle cap 24. The fin 72 is also near the needle port 76 through which the needle 30 extends. The fin 72 is also located adjacent the mounting location 90 where the V-clip 58 will be located when mounted in the needle cap 24. Ideally, the fin 72 is positioned between the V-clip 58 and the needle port 76 when the V-clip 58 is mounted within the needle cap 24. The fin 72 may be formed of any low friction material described herein, such as a low friction polymer.

Figure 6:
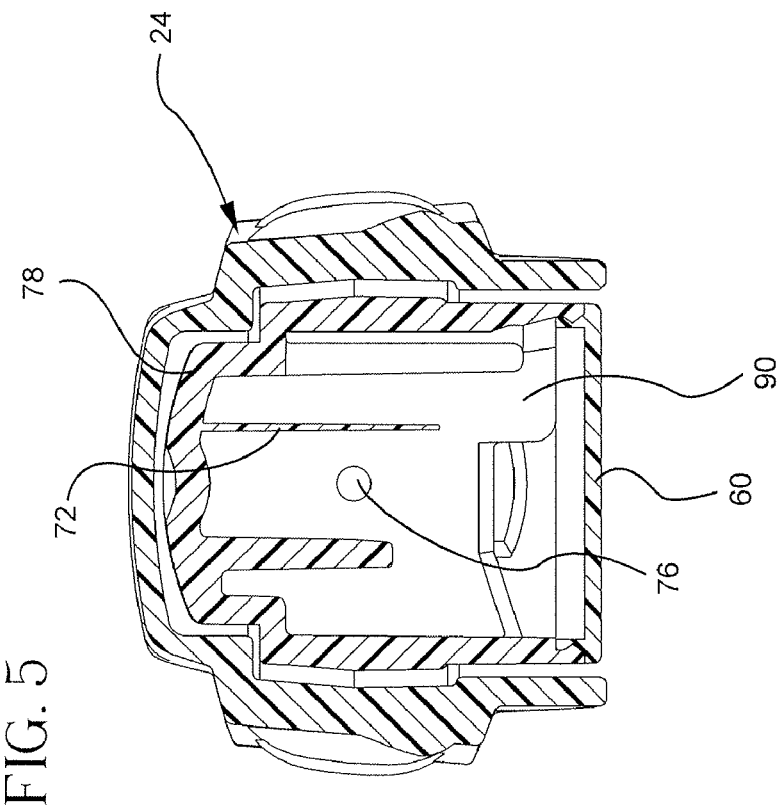
FIG. 6 is a cross section simulation view of the operation of a portion of a needle cap.

Referring to FIG. 6, a simulation of the interior of a needle cap 24 having a fin 72 is illustrated. The simulation illustrates the V-clip 58 both before and after activation, in both its compressed and expanded states. In its compressed state, the V-clip 58 is separated from the outer surface of the needle 30 by means of the fin 72. After the needle 30 is removed from the needle port 76, the V-clip 58 is activated, causing the first arm 62 to extend away from the second arm 64. The first arm 62 will extend past the needle port 76, causing the fin 72 to also move past the needle port 76 and into an appropriate window or resting location for the fin 72.

Referring to FIG. 7, a second stage of the simulation described with reference to FIG. 7 reveals the various components of the needle cap 24 after the V-clip 58 has been engaged and the needle 30 has been removed from the needle port 76. In its engaged state, the V-clip 58 has moved such that the second arm 64 has moved towards the needle port 76, the first arm 62 has moved beyond the needle port 76, and the fin 72 has been moved by the first arm 62 and an elbow 80 between the first arm 62 and a second arm 64 in a direction past and beyond the needle port 76 and into a window or space where the fin 72 may reside.

The fin 72 needs a space in which to reside, such as a window and/or a groove, as will be described below, in order to permit the first arm 62 of the V-clip 58 to move along its entire range of motion necessary to release the pawl 68 from any corresponding groove or locking mechanism to which it may be attached. If the movement of the pawl 68 is restricted due to the fin 72 and therefore unable to move sufficient to release an engaged portion of the catheter adapter 18, then additional force will be needed to remove the catheter adapter 18 from the needle clip 24. In attempting to separate the catheter adapter 18 from the needle clip 24 without the pawl 68 being disengaged, damage to the V-clip 58, the catheter adapter 18 and/or the patient may occur. Thus, by permitting the fin 72 to move into an accommodating space, the first arm 62 of the V-clip 58 is able to fully open, causing the pawl 68 to fully disengage from a catheter adapter 18.

Referring to FIG. 8, a cross section view of the catheter assembly 10 is shown revealing a cross section view of the needle cap 24 and its internal components. The interior of the needle cap 24 reveals the V-clip 58 compressed such that the first arm 62 is substantially parallel with the second arm 64 and the fin 72 is located between the face of the first arm 62 and the outer surface of the needle 30 which is located within the needle port 76. The cross section view of the catheter assembly 10 also reveals the protection cap 22 and the catheter adapter 18.

Figure 9:
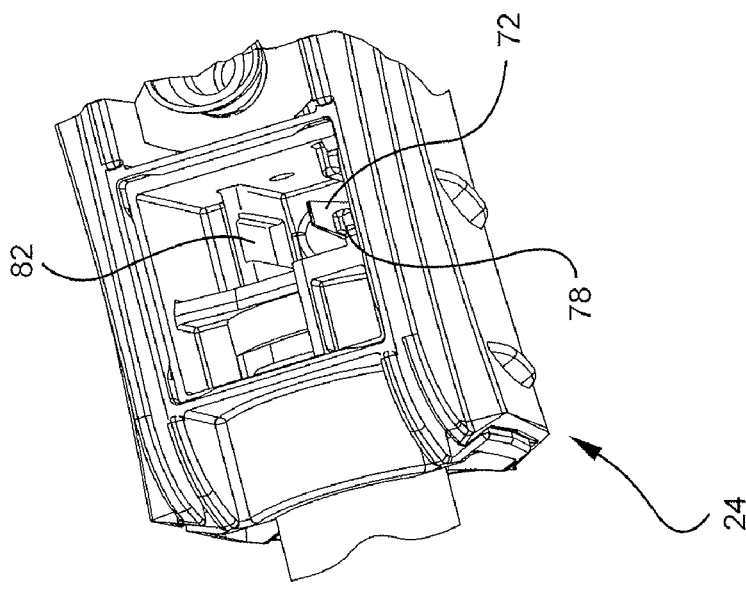
FIG. 9 is a bottom perspective view of a portion of a needle cap illustrating an alternate embodiment of the fin window.

Referring to FIG. 9, a bottom perspective view of the needle cap 24 is shown. The bottom view reveals the fin 72 integral and/or secured to the housing 78 of the needle cap 24. Also shown is a groove 82 that provides a space into which the fin 72 may reside when moved by the engaged V-clip 58.

Figure 10:
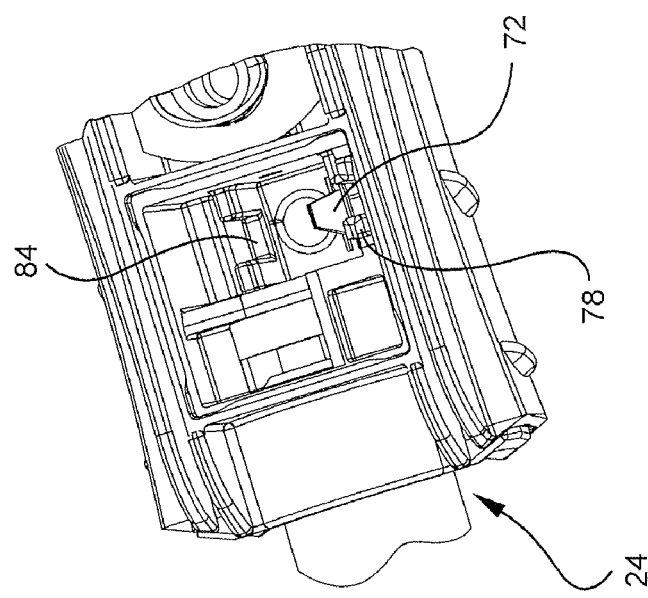
FIG. 10 is a bottom perspective view of a portion of a needle cap illustrating an alternate embodiment of the fin window.

Referring to FIG. 10, a bottom perspective view of another embodiment of a needle cap 24 is shown. The bottom view reveals a fin 72 on the underside of the housing 78 of the needle cap 24. The view also reveals a window 84 similar to the window previously described that is capable of providing a space into which the fin 72 may enter and reside after the fin 72 is moved by the structure of the engaged V-clip 58.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An extravascular system for accessing the vasculature of a patient, comprising:
   a catheter assembly;
   a needle; and
   a needle tip shield assembly having a needle cap, the needle cap having a V-clip needle shield wherein the V-clip includes a first arm and a second arm joined by an elbow, and a structure having at least one low friction surface;
   wherein the needle is disposed within the catheter assembly and the needle tip shield assembly; and
   wherein the structure having the low friction surface resides between the needle shield and the needle and wherein the withdrawal force of the needle is reduced by the structure.

2. The system of claim 1, wherein the structure is secured to the needle cap.

3. The system of claim 1, wherein the structure is integral to the needle cap.

4. The system of claim 1, wherein the structure includes a fin.

5. The system of claim 1, wherein the at least one low friction surface further comprises a lubricant.

6. The system of claim 1, wherein the at least one low friction surface includes a polymer.

7. The system of claim 1, wherein the at least one low friction surface is adhered to an adjoining structure.

8. The system of claim 1, wherein the at least one low friction surface includes a surface with smooth edges.

9. A method of manufacturing an extravascular system for accessing the vasculature of a patient, comprising:
   providing a catheter assembly;
   providing a needle;
   disposing the needle at least partially within the catheter assembly;
   providing a needle tip shield assembly having a needle cap, the needle cap having a needle shield;
   disposing the needle at least partially within the needle cap;
   preparing a structure having at least one low friction surface disposed between the needle shield and the needle such that the withdrawal force of the needle is reduced by the structure; and
   further comprising forming the needle shield as a V-clip having a first arm joined to a second arm by means of an elbow.

10. The method of claim 9, further comprising decreasing the withdrawal force and friction of the needle as it is drawn past the needle shield.

11. An extravascular system for accessing the vasculature of a patient, comprising:
   a catheter assembly means;
   a needle means; and
   a needle tip shield assembly means having a needle cap means, the needle cap means having a means for shielding a needle, said means for shielding a needle comprising a V-clip including a first arm and a second arm joined by an elbow and means for providing low friction;
   wherein the needle means is disposed within the catheter assembly means and the needle tip shield assembly means; and
   wherein the means for providing low friction comprises a structure residing between the means for shielding a needle and the needle means wherein the withdrawal force of the needle is reduced by the structure.

* * * * *